United States Patent [19]

Seeger

[11] Patent Number: 5,360,714
[45] Date of Patent: Nov. 1, 1994

[54] HEPADNAVIRUS POLYMERASE GENE PRODUCT HAVING RNA-DEPENDENT DNA PRIMING AND REVERSE TRANSCRIPTASE ACTIVITIES AND METHODS OF MEASURING THE ACTIVITIES THEREOF

[75] Inventor: Christoph Seeger, Melrose, Pa.
[73] Assignee: Fox Chase Cancer Center, Philadelphia, Pa.
[21] Appl. No.: 101,253
[22] Filed: Aug. 2, 1993

Related U.S. Application Data

[63] Continuation-in-part of Ser. No. 937,214, Aug. 28, 1992.
[51] Int. Cl.$^5$ ............... C12Q 1/48; C12Q 1/68; C08L 5/00; C12N 9/12
[52] U.S. Cl. ........................ 435/5; 435/15; 435/69.1; 435/91.51; 935/14; 935/17; 252/183.11; 536/23.2; 536/23.72
[58] Field of Search ............ 435/6, 15, 5, 69.1, 435/194, 91.51; 935/14, 17; 536/23.2, 23.72; 252/183.11

[56] References Cited

U.S. PATENT DOCUMENTS

| | | | |
|---|---|---|---|
| 4,937,074 | 6/1990 | Venkateswaran et al. | 424/195.1 |
| 4,968,674 | 11/1990 | Taniyama et al. | 514/63 |
| 4,997,926 | 3/1991 | Haertle et al. | 536/27.14 |

FOREIGN PATENT DOCUMENTS

| | | |
|---|---|---|
| 343133 | 11/1989 | European Pat. Off. |
| WO8800050 | 11/1988 | WIPO |
| WO9214839 | 9/1992 | WIPO |

OTHER PUBLICATIONS

T. Wu et al., J. Virol., 65: 2155-63 (1991).
H. Meisel et al., J. Med. Virol., 30: 137-141 (1990).
L. Chang et al., J. Virol., 64: 5553-58 (1990).
G. Civitico et al., J. Med. Virol., 31: 90-97 (1990).
W. Offensperger et al., Virology, 164: 48-54 (1988).
H. Lin et al., J. Med. Virol., 12: 61-70 (1983).
C. Howard, J. Med. Virol., 3: 81-86 (1978).
P. L. Marion, Current Topics in Microbiology and Immunology, 168: 168-183 (1991).
M. Bavand et al., J. Virol., 63: 1019-1021 (1989).
E. Mandart et al., J. Virol., 49: 782-792 (1984).
J. C. Pugh et al., J. Virol., 62: 3513-3516 (1988).
L. Chang et al., Nature, 337: 364-368 (1989).
H. Schlicht, Cell, 56: 85-92 (1989).
M. Bavand et al., J. Virol., 62: 626-628 (1988).
R. Bartenschlager et al., Nucleic Acids Research, 20: 195-202 (1992).
C. G. Lin et al., Virology, 188: 342-352 (1992).
E. McGlynn et al., J. Gen. Virol., 73: 1515-1519 (1992).
H. G. Kochel et al., Virology, 182: 94-101 (1991).
G. Foster et al., Proc. Natl. Acad. Sci. USA, 88: 28882892 (1991).
D. Ganem et al., Ann. rev. Biochem., 56:651-93 (1987).
M. Junker-Niepmann et al., The EMBO Journal, 9: 3389-3396 (1990).
K. L. Molnar-Kimber et al., J. Virol., 51: 181-191 (1984).
C. Seeger et al., Science, 232: 477-484 (1986).
C. Seeger et al., J. Virol., 64: 16-23 (1990).
C. Seeger et al., J. Virol., 65: 5190-5195 (1991).
J. Summers et al., Cell, 29: 403-415 (1982).
J. Tavis et al., Biochemistry, 90: 4107-4111 (1993).
J. Tuttleman et al., Cell, 47: 451-460 (1986).
R. Hirsch et al., Nature, 344: 552-555 (1990).
G.-H. Wang & C. Seeger, Cell, 71: 663-70 (1993).

*Primary Examiner*—Robert A. Wax
*Assistant Examiner*—Rebecca Prouty
*Attorney, Agent, or Firm*—Dann, Dorfman, Herrell and Skillman

[57] ABSTRACT

An enzymatically active composition of matter, comprising an extracellular combination of a substantially virus-free hepadnavirus polymerase gene product and an RNA template for hepadnavirus minus strand DNA synthesis, is provided. The composition possesses a DNA priming activity and a reverse transcriptase activity. The hepadnavirus polymerase gene product is produced by in vitro expression of a hepadnavirus pol gene.

The enzymatically active composition of matter is used in rapid in vitro assays to screen potential anti-hepadnaviral agents. Assays for various functions of the hepadnavirus DNA polymerase are provided, including: (1) binding of the polymerase gene product to hepadnavirus pre-genomic RNA; (2) DNA priming activity of the polymerase gene product; and (3) reverse transcriptase activity of the polymerase gene product.

18 Claims, 5 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 85 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: duck hepatitis B virus (DHBV)

( i x ) FEATURE:
( A ) NAME/KEY: proteinbind
( B ) LOCATION: 4..7
( D ) OTHER INFORMATION: /function="REVERSE TRANSCRIPTASE INITIATION OF MINUS STRAND DNA SYNTHESIS"
/ boundmoiety="HEPADNAVIRUS POLYMERASE GENE PRODUCT"

( i x ) FEATURE:
( A ) NAME/KEY: proteinbind
( B ) LOCATION: 43..46
( D ) OTHER INFORMATION: /function="BINDING/DNA PRIMING"
/ boundmoiety="HEPADNAVIRUS POLYMERASE GENE PRODUCT"

( x i ) SEQUENCE DESCRIPTION: SEQ ID NO:1:

GAAUUACACC CCUCUCCUUC GGAGCUGCUU GCCAAGGUAU CUUUACGUCU ACAUUGCUGU    60

UGUCGUGUGU GACUGUACCU UGGUA    85

HEPADNAVIRUS POLYMERASE GENE PRODUCT HAVING RNA-DEPENDENT DNA PRIMING AND REVERSE TRANSCRIPTASE ACTIVITIES AND METHODS OF MEASURING THE ACTIVITIES THEREOF

Pursuant to 35 U.S.C. §202(c), it is hereby acknowledged that the U.S. Government has certain rights in the invention described herein, which was made in part with funds from the National Institutes of Health.

This application is a continuation-in-part of co-pending U.S. patent application Ser. No. 07/937,214, filed Aug. 28, 1992.

FIELD OF THE INVENTION

The present invention relates to the development of anti-viral therapy for chronic hepadnavirus infection. In particular, the invention relates to a hepadnavirus polymerase gene product, produced in vitro and having RNA-dependent DNA priming and reverse transcriptase activities, and to the use of said gene product for rapid in vitro assays to screen potential anti-viral agents.

BACKGROUND OF THE INVENTION

Hepatitis B is a life-threatening disease that affects millions of individuals worldwide. Several vaccines are currently available to prevent initial infection with the hepatitis B virus (HBV). However, many patients become chronically infected with the virus, becoming potential sources of spread of the disease, and suffering the high risk of liver ailments associated with long-term infection, such as chronic hepatitis, cirrhosis and hepatocellular carcinoma.

Chronic hepadnavirus infection is extremely difficult to eradicate for several reasons: (1) chronically infected patients develop immunotolerance to viral surface antigens; (2) the hepatitis B virus does not kill host hepatocytes, so viral infection cannot be overcome simply by preventing new infection and allowing already-infected host cells to die; (3) the covalently closed circular form of the hepadnavirus genome does not self-replicate and is therefore unaffected by agents which inhibit DNA-directed DNA synthesis; (4) hepatitis B virus exists in non-hepatic tissues, so reinfection of hepatic tissue may result from virus located in other tissues; and (5) the hepadnavirus genome can integrate into hepatocyte chromosomes, and thus exist in a dormant, non-replicative form for many years. See P. L. Marion, Current Topics in Microbiology and Immunology, Vol. 168: 167–183 (1991). In spite of these obstacles, certain steps in the replication cycle of hepadnaviruses have been cited as potential targets for anti-viral therapy. One potential target is the replication of the hepadnavirus genome by reverse transcription of the RNA pregenome. This step is essential in the life cycle of the virus.

Reverse transcription of the RNA pregenome is catalyzed by a gene product encoded by the hepadnavirus pol gene. The pol gene encodes three activites: (1) DNA priming activity; (2) reverse transcriptase (i.e., RNA-directed DNA polymerase) activity; and (3) RNAse H activity. It has heretofore not been known whether these three catalytic functions are embodied in one or several separate gene products. In fact, little is known about the product or products of the viral pol gene, and this lack of knowledge has frustrated attempts to develop anti-viral agents targeted to the pol gene product.

Efforts to obtain more detailed information about the mechanism and biochemistry of the reactions directing reverse transcription of the hepadnavirus genome have been stymied by the inability to obtain enzymatically active hepadnavirus polymerase gene product. See, e.g., Bayand et al., J. Virol., 63: 1019–21 (1989). Consequently, there has been no feasible means to study or screen for anti-viral agents directed toward this protein or set of proteins. Thus, a potentially useful target for anti-viral therapy has remained virtually unexplored. A need clearly exists for the production of a purified hepadnavirus polymerase gene product that can be used for in vitro assays to screen for potential anti-viral agents. A concomitant need exists for methods to measure the various activities of such a gene product, once it becomes available.

SUMMARY OF THE INVENTION

In accordance with the present invention, a composition of matter comprising, in extracellular combination, a substantially virus-free hepadnavirus polymerase gene product and an RNA template for hepadnavirus minus strand DNA synthesis is provided. The composition of matter comprising the aforementioned extracellular combination possesses a DNA priming activity and a reverse transcriptase activity. In a preferred embodiment, the hepadnavirus polymerase gene product is produced by expression, in a non-hepadnavirus system, of a purified and isolated DNA sequence encoding the hepadnavirus polymerase gene product. In a particularly preferred embodiment of the present invention, the RNA template for hepadnavirus minus strand DNA synthesis is the same RNA as the transcript produced by in vitro transcription of the isolated DNA sequence, and thereafter translated into the hepadnavirus polymerase gene product.

According to another aspect of the present invention, a rapid, in vitro method for measuring the DNA priming activity of a hepadnavirus polymerase gene product is provided. The method comprises the steps of: (1) providing the above-described substantially virus-free hepadnavirus polymerase gene product; (2) providing an RNA template for hepadnavirus minus strand DNA synthesis, the template comprising a binding/priming site for the polymerase gene product; (3) combining, in an assay buffer, the polymerase gene product, the RNA template and a detectably-labelled nucleotide triphosphate comprising the first nucleotide incorporated into the hepadnavirus minus strand DNA (usually dGTP), under conditions promoting the DNA priming activity of the polymerase gene product, resulting in the formation of a complex comprising the gene product and the detectably labelled nucleotide triphosphate; (4) separating the complex from the assay buffer; and (5) detecting the amount of detectably labelled nucleotide triphosphate in the separated complex, the amount of detectably labelled nucleotide triphosphate in the separated complex being indicative of the DNA priming activity of the hepadnavirus polymerase gene product.

According to another aspect of the present invention, the above-described method for measuring the DNA priming activity of a hepadnavirus polymerase gene product is adapted to a rapid, in vitro method of screening potential anti-hepadnaviral agents for the ability to inhibit such DNA priming activity.

According to another aspect of the present invention, there is provided a rapid, in vitro method for measuring the ability of a hepadnavirus polymerase gene product to bind to an RNA template for hepadnavirus minus strand DNA synthesis. The method comprises the steps of: (1) providing the above-described substantially virus-free hepadnavirus gene product; (2) providing a detectably-labelled RNA template for hepadnavirus minus strand DNA synthesis, the template comprising a binding site for the hepadnavirus polymerase gene product; (3) combining the polymerase gene product with the RNA template under conditions promoting the binding of the polymerase gene product to the RNA template, resulting in the formation of a complex comprising the polymerase gene product and the RNA template; (4) separating the complex from the assay buffer; and (5) detecting the amount of detectably-labelled RNA template in the separated complex, the amount of detectably-labelled RNA template in the separated complex being indicative of the ability of the hepadnavirus polymerase gene product to bind to the RNA template.

According to another aspect of the present invention, the above-described method for measuring the ability of a hepadnavirus polymerase gene product to bind to an RNA template is adapted to a rapid, in vitro method of screening potential anti-hepadnaviral agents for the ability to inhibit such binding.

According to yet another aspect of the present invention, a rapid, in vitro method for measuring the reverse transcriptase activity of a hepadnavirus polymerase gene product is provided. The method comprises: (1) providing the above-described composition of matter having DNA priming activity and reverse transcriptase activity; (2) combining in an assay buffer the composition of matter with nucleotide triphosphates for DNA synthesis, one of said nucleotide triphosphates optionally being detectably labelled, under conditions promoting the reverse transcriptase activity of the polymerase gene product, thereby producing a nascent strand of DNA from the RNA template, the DNA strand being part of a complex which further comprises the polymerase gene product; (3) separating the complex from the assay buffer; and (4) detecting the amount of the nascent DNA strand in the separated complex, that amount being indicative of the reverse transcriptase activity of the hepadnavirus polymerase gene product. The length of the nascent DNA strand may also be observed, which provides an additional indication of reverse transcriptase activity of the hepadnavirus polymerase gene product.

In a preferred embodiment of the aforementioned assay for reverse transcriptase activity, reverse transcriptase activity can be measured separate from DNA priming activity according to the following method: (1) an RNA template is provided that possesses the starting site for minus strand DNA synthesis, but not the binding site for the polymerase gene product, nor the site for DNA priming activity; (2) this template is combined with a substantially virus-free hepadnavirus polymerase gene product, as described above, which has already been incubated with an RNA template comprising the binding/priming site, thereby becoming pre-primed and capable of exerting a reverse transcriptase activity, under conditions promoting reverse transcriptase activity of the polymerase gene product, thereby producing a nascent strand of DNA from the RNA template, the DNA strand being part of a complex which further comprises the polymerase gene product. The amount and length of nascent DNA strand in the separated complex is then detected, as described above.

According to another aspect of the present invention, the above-described methods for measuring reverse transcriptase activity of a hepadnavirus polymerase gene product are adapted to rapid, in vitro method of screening potential anti-hepadnaviral agents for their ability to inhibit such reverse transcriptase activity.

The enzymatically active extracellular combination of a substantially virus-free hepadnavirus polymerase gene product and an RNA template for hepadnavirus minus strand DNA synthesis, along with the rapid, in vitro assays that utilize the composition of matter, provide an extremely useful and long-needed target for development of anti-viral agents directed to hepadnavirus replication. The compositions and methods of the present invention will allow the screening of many anti-viral compounds simultaneously, with ease and rapidity. Moreover, quantitative results of the effect of each potential anti-viral agent are easily obtained. Heretofore, such results have been unobtainable.

BRIEF DESCRIPTION OF THE DRAWINGS

The foregoing summary, as well as the following description of preferred embodiments of the present invention, will be better understood when read in conjunction with the appended drawings in which:

FIG. 2 is a set of autoradiographs of in vitro translation reactions and assays for DNA priming and reverse transcriptase activities of the DHBV polymerase gene product.

FIG. 5 is a schematic diagram depicting a physical map of the DHBV polymerase polypeptide. The positions of conserved amino acid residues are indicated. Tyrosine residue (Y) 96 is required for the formation of the covalent bond between the polymerase gene product and minus strand DNA. Glutamic acid (D) residues 446, 514 and 515 are essential for the catalytic activity of the polymerase. Glutamic acid residue 715 is required for the RNAse H activity of the polymerase gene product. The open rectangle depicts a spacer region whose function is unknown. The bars below the figure depict the domains of the polymerase polypeptide that are thought to be required for DNA priming and binding with the stem loop ε structure.

DETAILED DESCRIPTION OF THE INVENTION

The hepadnavirus polymerase gene product is referred to in the art by many different names. For purposes of the present invention, the following terminology will be applied. The product of the hepadnavirus pol gene is sometimes referred to herein as "hepadnavirus polymerase gene product", "polymerase gene product", "viral gene product" or "gene product". The polymerase gene product possesses a reverse transcriptase activity, among others. This catalytic function is also sometimes referred to herein as "RNA-directed DNA polymerase activity". The polymerase gene product, when produced by in vitro transcription/translation of a hepadnavirus pol gene, may also be referred to herein as an "in vitro translation product" or "translation product". Reference to the gene product as a translation product will be made only when describing the in vitro transcription/translation of the pol gene, which is a preferred method of making the polymerase gene product of the present invention.

Figure 1:
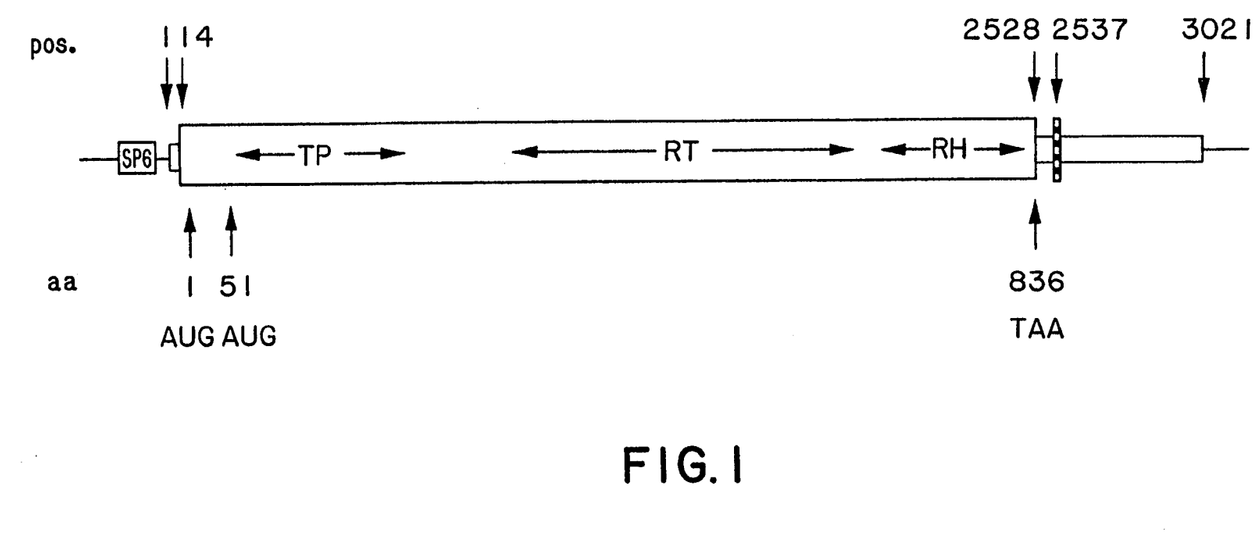
FIG. 1 is a schematic diagram of the structure and orientation of the duck hepatitis B virus (DHBV) genome, inserted into an in vitro transcription vector to form the plasmid p5.1Gal.
Figure 2A:
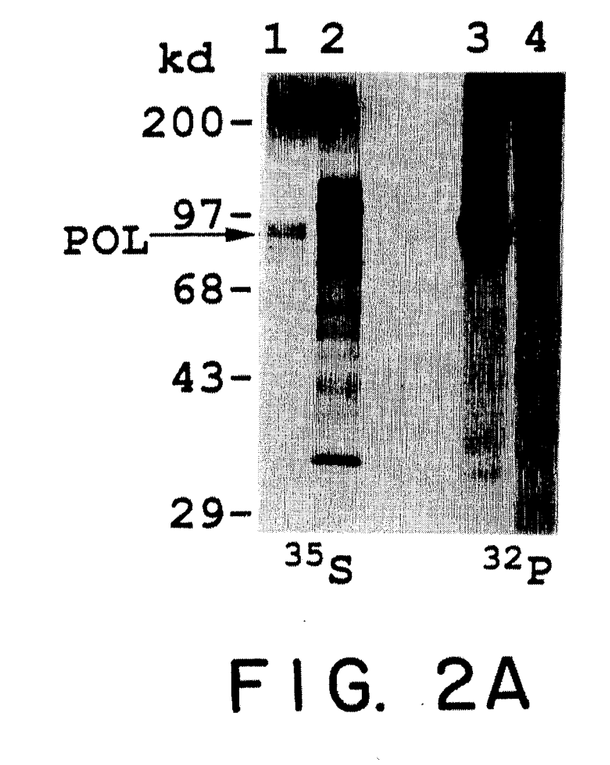
FIG. 2A: in vitro translation products (Lanes 1 and 2); assay of DNA priming function (Lanes 3 and 4)

In accordance with the present invention, an enzymatically active hepadnavirus polymerase gene product has now been obtained by in vitro transcription/translation of a hepadnavirus pol gene. The viral gene product was generated by SP6-promoted in vitro transcription of a plasmid containing a complete copy of an infectious duck hepatitis B virus (DHBV) genome (see FIG. 1), followed by in vitro translation of the resulting 3.1 kb RNA in a rabbit reticulocyte lysate in vitro translation system. As shown in FIG. 2A, the major in vitro translation product is a protein with an estimated molecular weight of 90 kDa, representing a 836 amino acid polypeptide (a faster-migrating translation product is also formed, presumably representing a 786 amino acid polypeptide translated from a start codon 51 amino acid downstream from the start codon of the major translation product).

Figure 2B:
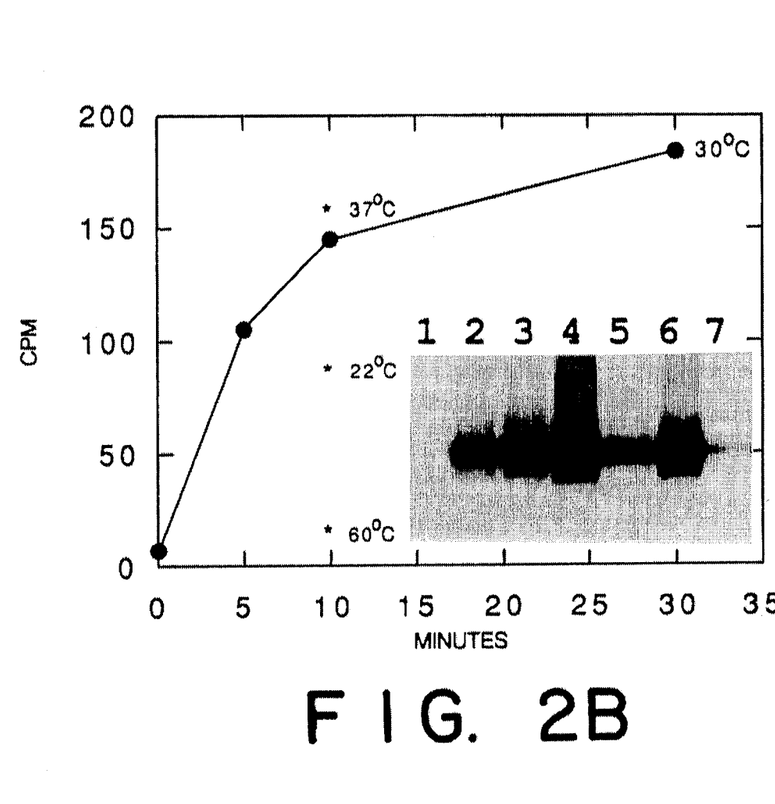
FIG. 2B: measurement of polymerase activity of DHBV polymerase gene product; graph is a quantitative representation of autoradiograph shown in inset; vertical axis=radioactivity incorporated in each band (cpm); horizontal axis=incubation time (minutes); filled circles=incubation time points at 30° C.; *=incubation temperatures at fixed, 10 minute incubation times.

As shown in FIG. 2A and 2B, the in vitro translation product was found to possess two catalytic functions: a DNA priming function and reverse transcriptase (i.e., RNA-directed DNA polymerase) activity, both of which were found to be dependent on the presence of the RNA template present in the in vitro translation (treatment of the in vitro translation product with ribonuclease abolished both the priming and polymerase activities) and magnesium ions. This RNA template is sometimes referred to herein as "cognate" RNA. As used herein, the term "cognate RNA" refers to RNA having part or all of the sequence that the hepadnavirus polymerase gene product requires to initiate and/or continue synthesis of minus strand DNA. As discussed below, the RNA dependence of the priming activity was unexpected, and could explain the failure of previous attempts by others to obtain an enzymatically active hepadnavirus polymerase gene product. See, e.g., Bayand et al., supra. The in vitro translation product is also expected to possess an RNAseH activity, which is a catalytic function possessed by the gene product in vivo.

Figure 3:
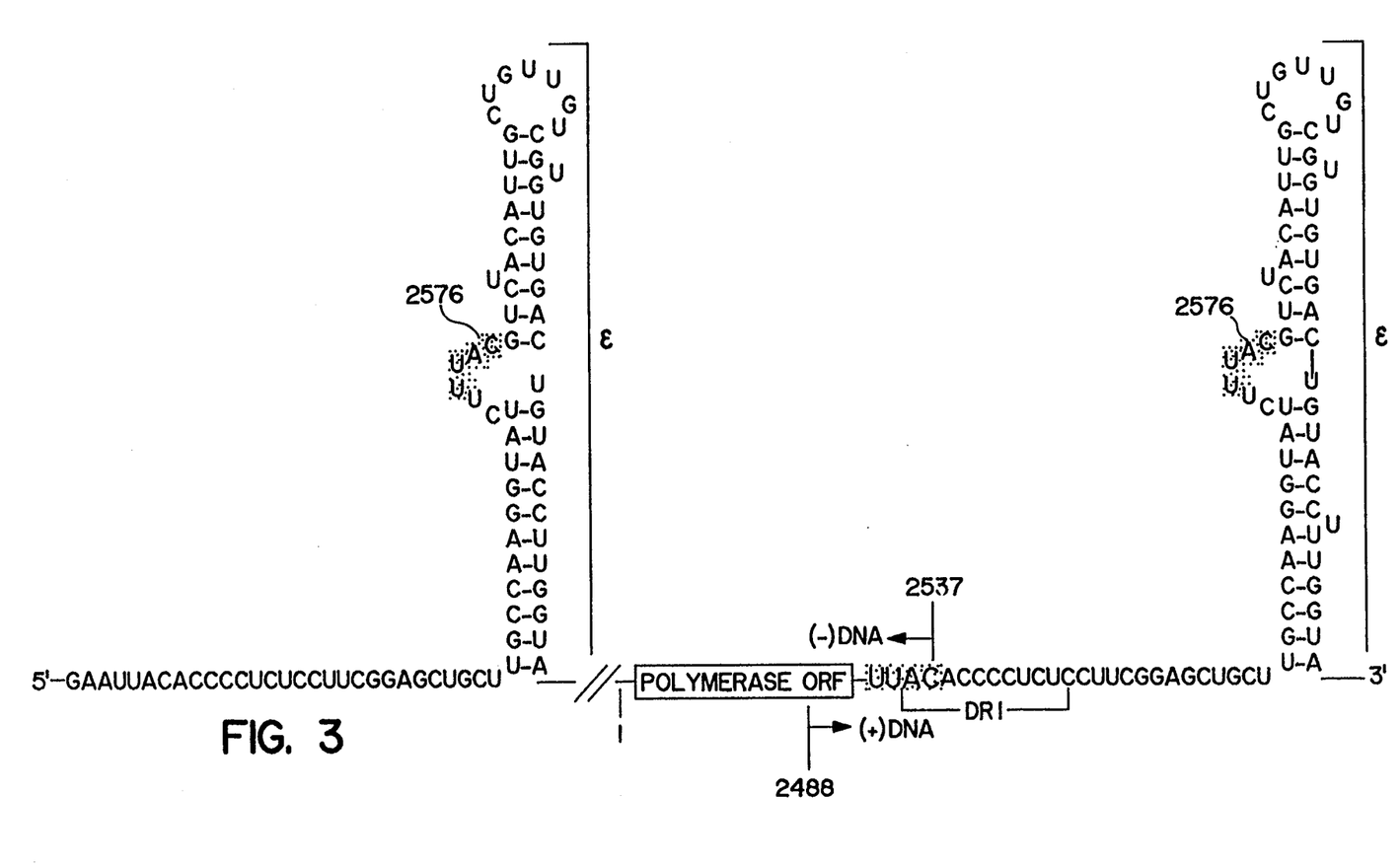
FIG. 3 is a schematic diagram of the structure of pre-genomic RNA of DHBV (the sequences of the two stem-loop structures are identical, except for an additional GAA at the 5' end of the first stem-loop structure; the stem-loop structure containing the additional 5' GAA=Sequence I.D. No. 1). The predicted stem-loop structure of e is depicted as described by Junker-Niepmann et al., EMBO J., 9: 3389-96 (1990). The positions of the polymerase open reading frame (ORF) and the 5' ends of minus and plus stranded DNAs are indicated. The UUAC motifs important for minus strand DNA synthesis at positions 2576 and 2537 are indicated. The DRI region, previously thought to be the initiation site for minus strand DNA synthesis, is indicated. The position of the 5' end of DHBV RNA used for expression of the polymerase in vitro is indicated (position 1). It should be noted that the RNA template used for the expression of the polymerase in vitro contains only one copy of ε at the 3' end.

The DNA genomes of hepadnaviruses are synthesized from an RNA template, which is the pregenome in subviral core particles (shown schematically in FIG. 3). Summers and Mason, Cell, 29: 403–15 (1982). Incorporation of pregenomic RNA into cores occurs by a mechanism that requires the binding of the viral polymerase to the RNA packaging (ε) signal which is located at the 5' end of pregenomic RNA. Hirsch et al., Nature, 344: 552–55 (1990); Junker-Niepmann et al., EMBO J., 9: 3389–96 (1990). The nucleotide sequence of ε contains a palindrome, which has the potential to fold into a stem-loop structure with a bulge and a loop (FIG. 3). Although the ε signal is located at both ends of the terminally redundant RNA template, it is the copy close to the 5' end of pregenomic RNA that exhibits activity for RNA packaging. However, minus strand DNA synthesis is initiated near the 3' end of pregenomic RNA. Seeger and Maragos, J. Virol., 64: 16–23 (1990).

Reverse transcription of all retroviruses and most retroid elements requires transfer RNA as a primer for DNA synthesis. In contrast, it has now been demonstrated in accordance with the present invention that the hepadnavirus polymerase gene product itself acts as the primer for reverse transcription, and that priming of minus strand DNA synthesis leads to the covalent attachment of the polymerase gene product to the 5' end of the nascent DNA strand. Surprisingly, the in vitro reaction conducted with the above-described hepadnavirus polymerase gene product revealed that DNA synthesis often arrested following the synthesis of a 4-nucleotide DNA oligomer with the sequence 5'dG-dT-dA-dA. This motif is identical with sequences on pregenomic RNA that correspond to the 5' end of minus strand DNA and is critical for correct initiation of DNA synthesis (FIGS. 1 and 3, pos. 2537). Moreover, identification of the 5' ends of in vitro synthesized minus strand DNA revealed that, in addition to the normal initiation site, a second site was used for DNA synthesis, which was located in the bulge region of the stem-loop structure of ε (FIG. 3, pos. 2576).

To determine which of the two sites provided the template for the initiation reaction, mutations were introduced into both sequences to examine their effects on the order of nucleotides incorporated into the reverse transcriptase. Following the translation reaction, the polymerase was incubated with solutions that contained all four dNTPs, one of which was labelled with $^{32}P$. As expected from the predicted nucleotide sequence at the 5' end of minus strand DNA expressed with a wild-type plasmid (5'-dG-dT-dA-dA-3'), incubation with $^{32}P$ labelled dGTP, dTTP or dATP, but not $^{32}P$ dCTP, yielded polymerase polypeptides that had acquired radioactivity. However, when the polymerase was expressed from a plasmid in which the UUAC motif located at position 2576 in the bulge had been changed to GGAC, the polymerase now incorporated $^{32}P$-dCMP instead of $^{32}P$-dAMP. Confirmation of this result was obtained with a second construct, in which the C residue at position 2576 was changed to G. This base change led to the incorporation of $^{32}$P-dCMP into the polymerase while the reaction with $^{32}$P-dGTP did not yield a labelled polymerase polypeptide.

These observations suggested that the UUAC motif located in the bulge of the ε signal provided the template for the synthesis of the first 4 nucleotides of minus strand DNA and that subsequently, the polymerase-dNMP complex translocated to the previously identified initiation site for minus strand DNA synthesis to continue DNA synthesis. This model implies that the 5' end of minus strand DNA is not collinear with the corresponding sequence on pregenomic RNA and predicts that a mutation introduced into the UUAC motif in the ε signal (pos. 2576) would lead to an identical base change at the 5' end of minus strand DNA (pos. 2537). Therefore, an experiment was conducted in which this site in ε at the 5' end of pregenomic RNA, which is required for RNA packaging in vivo, was changed from UUAC to UCAC. In agreement with the aforementioned model, the resulting progeny virus possessed genomes in which the T residue at position 2535 was changed to C. Independent confirmation of this result was obtained with a second plasmid. In this plasmid, the UUAC motif at position 2537 was changed to UUAA, while the motif in the ε signal remained unchanged. The nucleotide sequence of the amplified DNA from the progeny virus in this case revealed that as a consequence of DNA replication, the A residue at position 2537 reverted back to C.

Figure 4A:
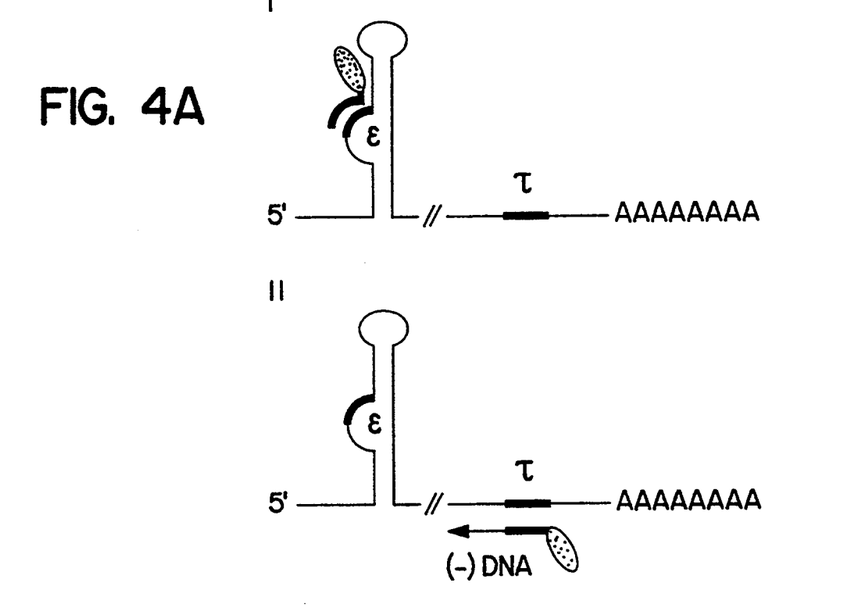
FIGS. 4A and B are a schematic diagram depicting a model for priming and initiation of minus strand DNA synthesis, developed in accordance with the present invention: (A) priming of reverse transcription of the hepadnavirus genome occurs at the 5' end of the pre-genomic RNA; (B) comparison of the nucleotide sequence of DHBV with the mammalian hepadnavirus HBV, WHY and GSHV in the bulge region of ε and at the initiation site for minus strand DNA synthesis.

Based on the foregoing two independent lines of evidence, a model for the replication of the hepadnavirus genome is proposed in accordance with the present invention. As shown schematically in FIG. 4A, this model predicts that the reaction which leads to the priming for reverse transcription of minus strand DNA synthesis employs RNA sequences present in the RNA packaging signal (ε) as a template for the polymerization of a short 4-nucleotide long DNA strand. Following the synthesis thereof, the nascent DNA strand switches templates to reanneal with the sequences on pregenomic RNA that correspond to the 5' end of minus strand DNA. Following this event, DNA synthesis can continue toward the 5' end of pregenomic RNA. Thus, the priming reaction occurs in two biochemically distinct steps: In the first, an amino acid residue of the polymerase (discovered in accordance with the present invention, to be tyrosine, as described below) acts as the primer for the formation of a covalent bond between protein and dGMP. In a second step, the G residue is extended through the addition of 3 nts to create the actual primer for minus strand DNA synthesis.

Figure 4B:
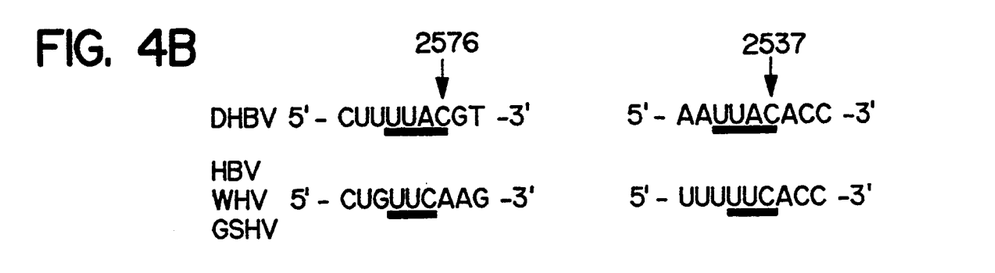

Although the results described above were obtained with an arian hepadnavirus, they are expected to be applicable to their mammalian counterparts, since replicative features are highly conserved among hepadnaviruses. In the present case, as shown in FIG. 4B, genetic analyses of the initiation site for reverse transcription of woodchuck hepatitis virus (WHV) had shown that a UUC sequence motif is sufficient to specify the 5' end of minus strand DNA. Seeger and Maragos, J. Virol., 65: 5190–95 (1991). As expected from the present model, the same sequence motif is indeed located in the bulge of the ε signal of the mammalian hepadnavirus genomes, exactly at the position corresponding to the UUAC motif found in DHBV. Junker-Niepmann et al., supra.

The above-noted similarity in sequence motif at the ε signal (sometimes referred to herein as the binding and/or priming site for the polymerase gene product) reflects the well-known commonality of replicative features within the closely-related group of hepadnaviruses. Since the seminal finding of Summers and Mason, Cell, 28: 403–15 (1982) that replication of DHBV proceeds by way of an RNA intermediate, DHBV has been used as a highly predictive model system (e.g., Molnar-Kimber et al., J. Virol., 51: 181–91, 1984; Tuttleman et al., Cell, 47: 451–60, 1986) for the elucidation of the replication cycle of hepadnaviruses as a class. See, e.g., Seeger et al., Science, 232: 477–83 (1986); Ganem and Varmus, Ann. Rev. Biochem., 56: 651–93 (1987). The aforementioned results obtained with DHBV are therefore expected to apply to hepadnaviruses as a class.

The results described above demonstrate that in hepadnaviruses the reactions leading to RNA packaging and reverse transcription are controlled by the same signal on pregenomic RNA. Since pregenomic RNA also acts as a mRNA template for the translation of the polymerase polypeptide the reverse transcriptase could bind to the ε signal during or immediately following translation. This model explains why pregenomic RNAs that express active polymerase polypeptides are preferred substrates for reverse transcription that RNAs with defective polymerase genes. Hirsch et al., supra; Wu et al., J. Virol., 65: 2155–63 (1991).

To substantiate the foregoing model for the replication of the hepadnavirus genome, it has been demonstrated in accordance with the present invention that the stem-loop ε structure alone is necessary and sufficient to activate the hepadnavirus polymerase gene product to initiate DNA minus strand synthesis. As a preliminary matter, to ascertain that no other sequences between the 4-nucleotide sequence at position 2537 and the stem-loop ε structure are required for minus strand DNA synthesis, the polymerase gene product was expressed from RNA templates with different deletions downstream of the polymerase gene. RNA segments between the pol gene and ε, as well as downstream of ε, did not appear to influence the activity of the enzyme to incorporate dGMP, the first nucleotide of minus strand DNA. However, polymerase polypeptides expressed from RNA templates that did not encode the complete ε motif failed to display this priming activity.

To directly test whether ε was sufficient for the enzymatic activity of the polymerase gene product, the polymerase was expressed from an RNA template that lacked sequences downstream of the polymerase and was therefore not capable of initiating minus strand DNA synthesis. The activity of the polymerase could, however, be restored when ε was provided to the in vitro translation reaction in trans.

The activity of the reverse transcriptase depended upon the concentration of ε and was maximal when the RNA was at least in a 100-fold molar excess over the polymerase polypeptide. The activity of the polymerase increased in a linear fashion when ε was present in a 1–10 molar excess. In agreement with previous experiments discussed above, the activity of the polymerase was more than 10-fold higher under conditions where ε was present during the in vitro translation reaction, as compared to conditions where it was added following expression of the polypeptide. To further confirm these results, the polymerase was next expressed from an RNA template that contained ε and was therefore enzymatically active. Incubation of this translated polymerase with ribonuclease abolished the ability of the enzyme to initiate minus strand DNA synthesis. However, this effect could be reversed by adding back the ε motif to the reaction. These results demonstrate that ε is required and sufficient for the activity of the hepadnavirus polymerase gene product to initiate minus strand DNA synthesis. Furthermore, the results suggest that the polymerase forms a complex with ε during or immediately after translation of the polypeptide.

To ascertain the nature of the ribonucleoprotein complex formed between ε and the hepadnavirus polymerase gene product, the following experiments were conducted. The polymerase was expressed in the presence of labelled RNA, and the amount of labelled RNA bound to the polymerase gene product was detected following immunoprecipitation of the polypeptide with a monoclonal antibody. The results showed that the polymerase gene product appeared to form a stable complex with ε and that ε remained bound to the polymerase following incubation with dNTPs. As expected, the enzymatic activity of the polymerase, as well as the formation of the ribonucleoprotein complex, were both dependent on the nucleotide sequence of ε. For example, when the DHBV ε was substituted with its HBV counterpart (see FIG. 4) the polymerase was unable to incorporate dGMP and did not form a complex with ε. Additionally, the inclusion of ε during the translation reaction again yielded significantly more active reverse transcriptase than addition of the RNA following the translation reaction. Similarly, when the in vitro expressed polymerase was incubated with labelled RNA, the amount of bound RNA was reduced approximately 10-fold, compared to conditions where ε was present during the translation reaction. These results demonstrate that the hepadnavirus polymerase gene product forms a complex with RNA comprising the ε sequence motif. The ribonucleoprotein complex (RNP) is sufficiently stable to remain intact under conditions used for immunoprecipitation.

The aforementioned model for priming of reverse transcription predicts that a tyrosine residue at position 96 of the DHBV polymerase is the substrate for the incorporation of the first nucleotide, dGMP, and that the template for this reaction is located in ε. For this reason, it is likely that the binding of ε with the polymerase polypeptide occurs through domains at the catalytic site of the enzyme, as well as in the amino terminal domain close to tyrosine 96. To identify potential binding sites, polymerase polypeptides with truncations at the amino- and carboxyl-termini were assayed for their enzymatic activity and ability to form a complex with ε.

Figure 5:
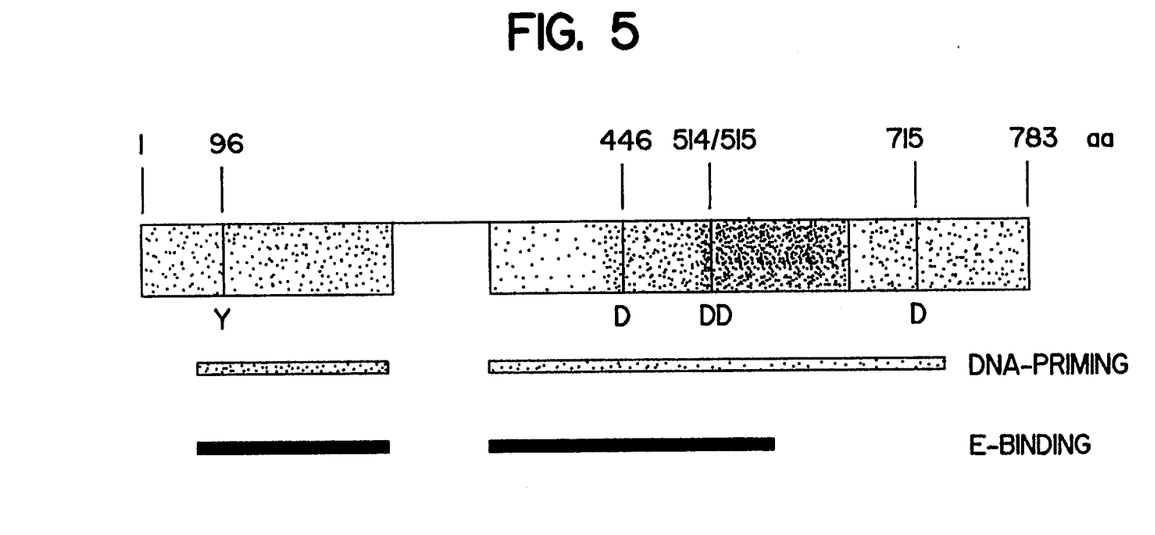

The activity of the polymerase to incorporate dGMP was lost when deletions extended into domain that are known to be required for DNA polymerase activity or for the priming of DNA synthesis (see FIG. 5). However, removal of a portion of the carboxyl-terminal RNAseH domain as well as a deletion of 67 amino acids in the amino-terminal domain of the polypeptide did not abolish enzymatic activity.

The ability of the polymerase to form a complex with ε was also dependent on the presence of both amino- and carboxyl-terminal domains of the polypeptide. The binding activity was lost when the N-terminal domain was truncated beyond tyrosine 96, the site for linkage between protein and DNA. In contrast to the requirements for enzymatic activity, RNP formation still occurred with a polymerase polypeptide lacking 226 amino acids from the carboxyl-terminus. However, the binding activity was lost in variants with deletions spanning beyond a conserved YMDD amino acid motif at residue 540 (not shown on FIG. 5), which is in the catalytic site of the polymerase domain.

The foregoing experimental protocols and results clearly demonstrate the unique relationship between the hepadnavirus polymerase gene product and specific primary and secondary signals on the hepadnavirus pre-genome required for genome replication. In accordance with the present invention, each of these signals provides an important target for the development of effective anti-viral agents for the treatment of chronic hepatitis infection, as described in greater detail hereinbelow.

The detailed description set forth below describes preferred methods for making and using the hepadnavirus polymerase gene product of the present invention. Novel assays for measuring the various activities of the purified polymerase gene product, which rely on unique aspects of the gene product, are also described. Any molecular cloning and recombinant DNA techniques not specifically described are carried out by standard methods, as generally set forth, for example, in Sambrook et al., "DNA Cloning, a Laboratory Manual", Cold Spring Harbor Laboratory (1989).

The hepadnavirus polymerase gene product of the present invention is preferably prepared from a purified, isolated DNA molecule comprising a sequence which encodes the gene product. Thus, any hepadnavirus pol gene will provide a suitable starting material for in vitro synthesis of the gene product. These include pol genes from human hepatitis B virus (HBV), duck hepatitis B virus (DHBV) and woodchuck hepatitis virus (WHV), among others.

The pol gene can be maintained in any common cloning vector, such as a plasmid, and maintained in an appropriate host cell, such as E. coli. Such cloning vectors may comprise a pol gene alone, or an entire hepadnavirus genome, which contains the pol gene and other viral genes. In a preferred embodiment, a plasmid vector containing an entire infectious hepadnavirus genome, positioned downstream from a bacteriophage promoter such as SP6, T7 or T3, is utilized as the starting material for preparation of the viral polymerase gene product. In a particularly preferred embodiment, the entire genome of infectious DHBV, contained in plasmid p5.1Gal, is used to produce a DHBV polymerase gene product. This embodiment is described in greater detail in Examples 1 and 2 below.

It should be apparent to those skilled in the art that DNA and RNA are both precursors for the ultimate polymerase gene product, and that the synthesis of an RNA molecule is an intermediate step in the ultimate production of the gene product. DNA molecules are preferred as the starting material for synthesis of the polymerase gene product because of their stability, in comparison to RNA molecules, and their ease of maintenance in cloning vectors and microbial host cells. However, the DNA molecule is used to synthesize an RNA molecule, which itself can be purified and stored for use in producing the polymerase gene product.

In accordance with the present invention, the purified hepadnavirus polymerase gene product is synthesized by in vitro transcription/translation of the hepadnavirus pol gene as described above. The in vitro transcription/translation is preferably carried out in a cell-free system. For example, a pol gene or hepadnavirus genome may be inserted into an in vitro transcription vector carrying a bacteriophage promoter, such as SP6, T7 or T3. Such in vitro transcription vectors are commercially available (e.g., from Promega Biotech, Inc., Madison, Wis.). In vitro transcription may then be carried out by, e.g., an SP6 RNA polymerase, using standard methods. Kits for performing in vitro transcription are also commercially available (e.g., from Promega Biotech, Inc.). If a kit is used, in vitro transcription is performed according to the supplier's instructions.

In vitro transcription of a hepadnavirus pol gene or a hepadnavirus genome containing the pol gene results in the formation of an RNA transcript, which then may be subjected to in vitro translation to produce the polymerase gene product. It will be appreciated that the hepadnavirus gene product produced in this manner is substantially free of other hepadnaviral components, with which it would be associated in vivo.

In a preferred embodiment, the resulting transcript is a 3.1 kb RNA molecule encoding the DHBV polymerase gene product. RNA transcripts produced by in vitro transcription may be purified by standard methods and stored for later use, or they may be used immediately for in vitro translation. In either event, in vitro translation of polymerase gene transcript may be performed in commercially-available cell free translation systems, such as the rabbit reticulocyte lysate system or the wheat germ system, both commercially available (Promega Biotech, Madison, Wis.) according to the supplier's instructions. In a preferred embodiment, the RNA transcript of a DHBV pol gene, as described above, is utilized for in vitro translation in a rabbit reticulocyte lysate system. The resultant translation product is a ~90 kDa polypeptide having RNA-dependent DNA priming and reverse transcriptase activities. The SP6-promoted in vitro translation of the DHBV RNA transcript in a rabbit reticulocyte lysate system is described in greater detail in Example 2 below.

In vitro translation reaction mixtures, comprising the hepadnavirus pol gene RNA transcript and the polymerase gene product, may be used immediately for the activity assays described below, without further processing. Alternatively, the reaction mixtures, containing both the RNA template and the gene product, may be stored at −70° C. for future use. It is preferred to use the in vitro translation mixture without further purification of the gene product, because the mixture already contains the RNA transcript encoding the gene product, which also serves as the template required for the priming and reverse transcriptase activity of the product.

In the event that further purification of the polymerase gene product is desired, the protein may be purified from the other components of the in vitro translation mixture by any common method, e.g., by immunological means or by various column chromatography steps. The purified polypeptide may then be used immediately, or stored frozen for future use. It should be apparent to those skilled in the art, however, that if the gene product is purified away from the RNA transcript encoding it, the transcript, or another appropriate RNA template (as described below), must be added back when assaying for the template-dependent priming or reverse transcriptase activities of the gene product.

The hepadnavirus polymerase gene product may also be synthesized from the pol gene or from intact viral genomes by coupled in vitro transcription/translation in a procaryotic or eucaryotic cellular system. If this alternative is selected, the pol gene or viral genome containing the pol gene is placed in an appropriate expression vector, many of which are commercially available. The vector is introduced into the selected host cell, such as E. coli or yeast, using methods that are widely known, and strains which are commonly available, e.g., E. coli strain HB101 or DH5α or Saccharomyces cerevisiae strain S288C. Again, it will be appreciated that the polymerase gene product produced in this manner will be substantially free of other hepadnaviral components.

In vitro expression of the viral pol gene in cellular systems will result in the formation of a viral polymerase gene product. The resulting polymerase gene product may be purified from host cells and other components of the expression system by common purification means, as described above for cell-free translation. In vitro expression kits are commercially available (e.g., from BioLabs, Beverly, Mass.) which contain instructions for in vitro expression and purification of the resultant proteins. The polymerase gene product produced by procaryotic or eucaryotic expression systems may be used immediately for activity assays, or may be stored for future use. Again, it should be apparent to those skilled in the art that assays for priming and reverse transcriptase activity of the gene product must be supplemented with the RNA template for synthesis of hepadnavirus minus strand DNA if the template has been removed during purification of the gene product.

The RNA transcript that actually encodes the polymerase gene product in the aforementioned in vitro transcription/translation systems comprises all the primary and secondary signals apparently necessary for minus strand DNA synthesis, and is a preferred RNA template in the practice of the present invention. However, other templates (e.g., templates comprising only a portion of the pol gene transcript, or even synthetic templates comprising cognate sequences) will also be useful in the method of the invention, as long as they comprise the requisite sequences and/or secondary structure for the activity being measured. For example, templates for measuring reverse transcriptase activity (which presupposes that the requirements for priming activity must also be met) will preferably comprise the entire RNA from which the polymerase gene product was formed (i.e., the polymerase open reading frame, the initiation site for minus strand DNA synthesis and the stem-loop ε, which includes the site for reverse transcriptase binding and priming activity).

Binding of the polymerase gene product and the DNA priming activity can also be measured with the aforementioned full-length RNA templates. In an alternative embodiment, the priming or binding activity may be measured separately from the reverse transcriptase activity by using RNA templates comprising only the ε stem-loop structure containing the site for polymerase gene product binding and priming activity. Even though the aforementioned specific templates are preferred for the practice of the present invention, any RNA template that confers enzymatic activity in extracellular combination with a hepadnavirus polymerase gene product is contemplated for use in the present invention. Using the assays described hereinbelow, and in the Examples, anyone skilled in the art would easily be able to determine whether a particular template is capable of contributing to overall enzymatic activity of the hepadnavirus polymerase gene product.

In accordance with the present invention, methods have been developed for measuring the DNA priming and reverse transcriptase activities of the hepadnavirus polymerase gene product. These methods rely on two key elements, in accordance with the present invention: (1) the availability of adequate amounts of substantially virus-free hepadnavirus polymerase gene product, and (2) an appropriate RNA template.

It should also be noted that, in addition to the RNA template, magnesium ions appear to be required for the catalytic functions of the polymerase gene product. Most DNA polymerases have been found to require magnesium or other divalent cations for catalytic activity. Hence, it should be appreciated by those skilled in the art that other divalent cations (including, but not limited to, magnanese) may be substituted for magnesium in the practice of the present invention.

It was previously known that dGTP is the first nucleotide triphosphate to be incorporated into the minus strand DNA synthesized from the hepadnavirus RNA pregenome. In accordance with the present invention, it has been determined that the formation of a covalent bond between the polymerase gene product and dGTP is the first step in minus strand DNA synthesis in DHBV and other hepadnaviruses having G as the first minus strand nucleotide. The formation of the aforementioned bond is referred to as "DNA priming activity". It has now been discovered in accordance with the present invention that binding of the polymerase gene product and DNA priming occurs in the stem-loop $\epsilon$ structure heretofore considered only as the packaging signal. The biochemical events that occur at $\epsilon$ can be divided into two parts: (1) binding of the polymerase gene product to the bulge in the stem-loop structure (at position 2576 of DHBV, for example); and (2) formation of the 4-nucleotide primer/polymerase gene product complex that is subsequently translocated to a nearby site on the viral RNA, where reverse transcription continues to produce full length minus strand DNA (position 2537 of DHBV, for example). In vitro assays to measure each of these steps are described below.

Binding of the hepadnavirus polymerase gene product can be measured by a simple binding assay, in which the purified hepadnavirus polymerase gene product is incubated with an RNA template comprising a stem-loop $\epsilon$ structure which has been labelled by any standard means. Stable ribonucleoprotein complexes between the stem-loop structure and the polymerase gene product are detected by immunoprecipitating the complexes and measuring the incorporation of radiolabel. Such a measurement may be accomplished by polyacrylamide gel electrophoresis, which can also detect a mobility shift in the polymerase gene product as a result of complex formation with the stem-loop structure, or by other methods such as liquid scintillation counting. Because binding of the polymerase gene product to $\epsilon$ is apparently the first step for minus strand DNA synthesis, a simple binding assay such as the one described above will be extremely useful for screening anti-viral agents that inhibit this critical step.

A rapid in vitro assay for the DNA priming activity of the hepadnavirus polymerase gene product comprises combining the purified in vitro-synthesized gene product prepared as described above, with an appropriate template, e.g., part or all of the RNA transcript of the hepadnavirus pol gene, having a binding/priming site and detectably labelled dGTP (or analog thereof), under conditions promoting the formation of a covalent bond between the gene product and the dGTP. It should be understood that, in the event a hepadnaviral template is used that does not incorporate dGTP as the first minus strand nucleotide, dGTP should be substituted with the appropriate nucleotide triphosphate (sometimes referred to herein as dNTP, N being any nucleotide), or analog thereof. However, for simplicity, the description below will exemplify dGTP as the first nucleotide incoprated into the DNA minus strand.

The priming assay is performed in a suitable biological buffer, such as 50 mM Tris-HCl (pH 7-8), 10 mM $MgCl_2$, 100 mM NaCl, 5 mM KCl, for time periods ranging from 5 to 60 minutes at temperatures between 20° C. and 45° C. In a preferred embodiment, in vitro translation reaction mix contains both the polymerase gene product and the RNA transcript from which it was produced, is utilized in the assay; therefore, additional RNA template need not be added. The dGTP added to the assay mixture may be detectably labelled by any common method known in the art. For example, in a preferred embodiment, $^{32}$P-dGTP is used. Other detectably labelled dGTP useful in the present invention includes $^{35}$S, $^3$H or $^{14}$C-labelled dGTP, as well as biotinylated or otherwise modified dGTP analysis.

Because of the covalent binding of dGTP, the DNA priming activity results in the formation of a covalent complex comprising dGTP and the polymerase gene product. This complex remains intact even upon exposure to 1M KOH at 55° C., and can be subjected to SDS polyacrylamide gel electrophoresis. The assay is based on measuring the amount of such a complex formed under pre-determined reaction conditions, as described above. Incorporation of labelled dGTP into the complex can be measured in a variety of ways, which will be readily apparent to those skilled in the art. For example, an aliquot of the assay mixture may be subjected to polyacrimide gel electrophoresis and autoradiography, if a radiolabel is used. Under these conditions, the complex is electrophoretically separated from the RNA template and other components of the reaction mixture, and can be visualized by autoradiography. The amount of dGTP incorporated into the complex may be quantitatively determined, e.g., by scanning densitometry. Alternatively, the protein-dGTP complex may be separated from the other components of the reaction mixture by immunological or other affinity methods, or by centrifugation. The amount of detectably labelled dGTP present in the separated complex may then be measured by various means, depending on the type of detectable labels used. These methods include, for example, liquid scintillation counting, spectrophotometry or fluorometry. Other methods for separating and measuring detectably labelled proteinaceous complexes are available, and should be apparent to one skilled in the art.

The elongation of the 4-nucleotide primer in the DNA priming step may also be measured, using a modification of the aforementioned assay for DNA priming activity. In this assay, knowledge of the sequence of the 4-nucleotide primer is necessary. For example, if as for wild-type DHBV, the 4-nucleotide primer consists of dG-dT-dA-dA, addition of any of these nucleotides to the 4-nucleotide chain can be measured by providing that nucleotide in a labelled form in the above-described priming assay and providing any previously-added NTP in an unlabelled form. For example, as described above, incorporation of the first dGTP is quantitated by using dGTP in the assay mixture. Similarly, incorporation of the next nucleotide, dTTP in this case, can be quantitated by providing only labelled dTTP in the assay mixture and including unlabelled dGTP in the mixture. Incorporation of the two subsequent dATPs is measured by utilizing labelled dATP in the assay in acdition to unlabelled dGTP and dTTP.

The above-described assay for priming activity of the hepadnavirus polymerase gene product may be modified to measure the gene product's reverse transcriptase activity. This is accomplished simply by adding, along with the detectably labelled dGTP the other nucleotide triphosphates necessary for DNA synthesis (i.e., dATP, dCTP, dTTP and analogs thereof). For this assay, some appreciable length of RNA template for the DNA minus strand is required, along with the aforementioned structure and sequences required for binding and DNA priming activity. The reaction is carried out under conditions promoting the reverse transcriptase activity of the gene product. For example, reactions may be carried out at 30° C. to 45° C. for 5 to 60 minutes. Reverse transcriptase activity of the gene product results in the synthesis of a nascent DNA strand from the RNA template. This DNA strand is part of a covalent complex which also comprises the gene product. The complex is detectable, by way of the detectably labelled dGTP incorporated into the growing DNA strands by any conventional method allowing detection of labelled DNA, e.g., Southern blot analysis.

In an alternative embodiment of the assay for reverse transcriptase activity of the polymerase gene product, the detectable label may be incorporated in any one of the four nucleotide triphosphates added to the assay mixture. However, detectably labelled dGTP is preferred because it is the first nucleotide triphosphate to be incorporated into the nascent DNA strand in most hepadnaviruses, and as such, is covalently bound to the gene product, as described above. dCTP is least preferred as the detectably labelled nucleotide triphosphate because, in most hepadnaviruses, it is not incorporated in the growing DNA strand until several other nucleotide triphosphates have been incorporated. Therefore, except as otherwise provided for elongation assays, use of this nucleotide triphosphate as a detectable label may underestimate the priming and reverse transcriptase activities of the viral gene product.

In yet another alternative embodiment, the reverse transcriptase assay may be performed using no labeled dNTPs. The nascent DNA strand may be labeled later, using common methods, such as nick-translation.

Reverse transcriptase activity of the hepadnavirus polymerase gene product may also be measured separately from binding or priming activity. This is accomplished by providing a ribonucleoprotein complex that comprises the polymerase gene product already primed by incubation with the stem-loop $\epsilon$ structure described above, combined with an RNA template for minus strand DNA synthesis that contains the start site for minus strand synthesis, but not the stem-loop $\epsilon$ structure. By providing the primed polymerase gene product in trans to such a 3'-truncated RNA template, reverse transcriptase activity of the gene product can be measured independently of the normally preceding binding/priming reaction. Such an assay is useful for specifically targeting the reverse transcriptase step, such that anti-viral agents that inhibit that step can be identified.

As described for the DNA priming activity assay above, the nucleotide triphosphates may be detectably labelled with a radioactive molecule, such as $^{32}P$, or they may be biotinylated or otherwise chemically modified so as to be detectable. Several methods are available to detect reverse transcriptase activity, including: (1) Southern blot analysis, (2) polyacrylamide gel electrophoresis, followed by autoradiography, as described above, (3) PCR amplification of the nascent DNA chain, and (4) primer extension. Methods to accomplish all of these detection techniques are well known in the art. As with the DNA priming activity assay described above, the complex comprising the polymerase gene product and the nascent DNA strand may be separated from the other components of the assay mixture. As described above, this may be accomplished by centrifugation. Preferably, though, the complex may be separated by affinity chromatography, and particularly advantageously by the use of antibodies recognizing the polymerase gene product. Once separated, the detectable label incorporated in the complex may be detected and quantified by several common means, depending on the type of detectable label utilized. These include liquid scintillation counting, spectrophotometry and fluorometry, among others.

Certain of the above-described rapid in vitro method of measuring the DNA priming and reverse transcriptase activities of the purified hepadnavirus polymerase gene product are described in greater detail in Examples 3 and 4 below.

The purified hepadnavirus polymerase gene product and the in vitro assay methods for measuring its priming and reverse transcriptase activities, as described above, are used to great advantage in the screening and development of anti-hepadnaviral agents. The gene product and assays provide an in vitro method for determining the effectiveness of potential anti-viral agent targeted to the pol gene or the polymerase gene product. Rapid, in vitro screening methods for anti-viral compounds directed to the polymerase gene product heretofore have been unavailable, due to the inability to obtain a substantially virus-free hepadnavirus gene product having biological activity.

Thus, potential anti-viral agents may be rapidly screened in vitro for their ability to inhibit the hepadnavirus polymerase gene product's priming activity, or reverse transcriptase activity, or both. Screening may be directed to specific steps of DNA priming or reverse transcriptase activities, such as (1) binding; (2) incorporation of the first dNTP in priming; (3) elongation of the 4-nucleotide primer; (4) translocation to the nearby site on viral RNA; and (5) reverse-transcription of minus-strand DNA. For example, to examine the effect of potential anti-viral agents on binding of the polymerase gene product to the stem-loop $\epsilon$ structure, an assay mixture comprising the gene product is prepared. Aliquots of the mixture are distributed into a series of test sample vessels containing compounds or agents suspected of having anti-viral activity. A control sample is included, wherein an aliquot of the assay mixture is distributed to a sample tube containing no anti-viral agent. To measure the effect of the potential anti-viral agents on binding of the polymerase gene product, reactions are initiated by the addition of detectably labelled stem-loop $\epsilon$ structures, as described above, under conditions promoting formation of a stable complex between the stem-loop structures and the polymerase gene product.

To examine the effect of inhibitors on priming activity, an assay mixture comprising the gene product, the RNA template and magnesium ions in a suitable biological buffer may be assembled. Aliquots of the mixture are then distributed into a series of test sample vessels containing compounds or agents suspected of having anti-viral activity. A control sample is also included, wherein an aliquot of the assay mixture is distributed to a sample tube containing no anti-viral agent. To measure the effect of the various potential anti-viral agents on the DNA priming activity of the gene product, reactions are initiated by the addition of detectably labelled dGTP, as described above, under conditions promoting formation of a covalent bond between the dGTP and the viral gene product. An identical series of assay samples may be assembled to test the effect of the potential anti-viral compounds on the reverse transcriptase activity of the gene product. In this instance, all four nucleotide triphosphates are added to the reaction mixture, as described above, for the reverse transcriptase activity assay. These samples are incubated under conditions which promote the elongation of the nascent DNA strand synthesized from the RNA template. Following the incubation periods, the amount of detectable label incorporated into the gene product-DNA complexes formed may be quantitated as described earlier. The lengths of the nascent DNA strands may also be observed, as an additional indication of the inhibitory capability of the potential anti-viral agent.

In a preferred embodiment of the present invention, potential anti-viral agents directed specifically to reverse transcriptase activity of the polymerase gene product are screened by an assay capable of measuring reverse transcriptase separately from binding or priming activity. In this assay, an assay mixture comprising an RNA template, dNTPs and magnesium ions in a suitable biological buffer is prepared. Aliquots of the mixture are then distributed into a series of test sample vessels containing the compounds or agents suspected of having anti-viral activity. Again, a control sample is included that does not contain an anti-vital reagent. Reactions are initiated by the addition of a ribonucleoprotein complex containing the polymerase gene product that has been pre-incubated with stem-loop ε structures and dNTPs, thereby becoming fully primed and capable of exerting reverse transcriptase activity. The reaction is carried out under conditions promoting elongation of the nascent DNA strand synthesized from the RNA template. Following the incubation period, the amount of detectable label incorporated into the gene product-DNA complexes formed may be quantitated as described earlier. The length of the DNA strands again may be observed as an additional indication of the inhibitory capacity of the potential anti-viral agent.

In this manner, many potential anti-viral compounds may be screened at one time in a rapid, in vitro assay. The assay may be conveniently adapted to large-scale screenings, e.g., in 96-well microtiter plates and the like. Moreover, quantitative results of the effect of each potential anti-viral agent are easily obtained, whereas heretofore, such results have been unobtainable.

In an alternative embodiment, the effect of various agents and processes directed toward the hepadnavirus pol gene itself may also be measured. For example, the rapid, in vitro assays may be used to measure the effect of in vitro mutagenesis of the pol gene or the RNA template. Thus, the effect of gene therapy, i.e., methods which alter or disrupt the formation of the polymerase gene product at the gene level, may be tested. Clearly, the enzymatically active hepadnavirus polymerase gene product and assay methods of the present invention provide a much-needed avenue for developing anti-hepadnaviral agents targeted to a critical step in the hepadnavirus life cycle.

The following examples are provided to describe the invention in further detail. These examples are intended merely to illustrate and not to limit the invention.

EXAMPLE 1

SP6-Promoted In Vitro Transcription of the DHBV pol Gene

The duck hepatitis B virus (DHBV) pol gene was transcribed by SP6-promoted in vitro transcription, according to the following procedure. Plasmid p5.1Gal was utilized for in vitro transcription. This plasmid contains a complete genome of an infectious clone of DHBV, inserted downstream from an SP6 promoter. See, Mandart et al., J. Virol., 49: 782–92 (1984); Pugh et al., J. Virol., 62: 3513–16 (1988). A schematic diagram of the structure and orientation of the DHBV genome in p5.1Gal is shown in FIG. 1. FIG. 1 shows the structural arrangement of the polymerase open reading frame (open rectangle), which begins at the amino terminus with the terminal protein (TP) domain, followed by a spacer region and the DNA polymerase (RT) and RNaseH (RH) domains. The hatched vertical bar represents the initiation site for minus strand DNA synthesis at position 2537 on the DHBV genome (Mandart et al., supra). The filled in rectangle represents DHBV sequences flanking the polymerase gene. The location of the SP6 promoter used for transcription of the polymerase gene is shown upstream of the pol gene. The positions of the first two methionines and the last amino acid of the polymerase polypeptide are indicated at the bottom of the figure. The numbering of the positions shown on top of the figure corresponds to the published sequence of DHBV (Mandart et al., supra).

To transcribe the RNA template for the translation of the DHBV polymerase gene, p5.1Gal was linearized with the restriction endonuclease SalI. The transcription reaction was carried out as described in the protocol included in the MEGAscript kit (AMBION, Inc., Austin, Tex.). The transcription reaction contained 7 μl water, 2 μl 10X transcription buffer (AMBION, Inc., Austin, Tex.), 2 μl each of ATP, CTP, GTP and UTP (50 mM each), 1 μl linearized plasmid DNA, and 2 μl enzyme mix (SP6 RNA polymerase, AMBION, Inc.). The reaction was incubated for 3 hours at 37° C. Following the incubation, 1 μl of RNAse-free DNAseI (AMBION, Inc.) was added, and incubation was continued for 15 minutes at the same temperature. Reactions were stopped by adding 115 μl of RNAse-free distilled water and 15 μl of ammonium acetate stop solution (AMBION, Inc.) and mixing thoroughly. RNA was purified by extracting the reaction once with an equal volume of water or buffer-saturated phenol/chloroform, followed by precipitation of the RNA by adding 2.5 volumes ethanol and mixing well. Reactions were chilled for at least 15 minutes at −20° C., then microfuged for 15 minutes at maximum speed to pellet the RNA. Supernatant was removed and the pellet resuspended in 1.5 μl of RNAse-free distilled water.

In vitro transcription of the DHBV polymerase gene resulted in the formation of a 3.1 kb RNA transcript. This transcript was utilized for in vitro translation to produce the polymerase gene product.

EXAMPLE 2

In Vitro Translation of RNA Transcript Encoding the DHBV Polymerase Gene Product The 3.1 kb RNA transcript produced by in vitro transcription, as described in Example 1 above, was used for in vitro translation to produce the DHBV polymerase gene product. The in vitro translation was carried out in a rabbit reticulocyte lysate in vitro translation system, according to methods provided by the commercial supplier (Promega Biotech, Madison, Wis.). The translation reaction contained the following ingredients: 14 μl rabbit reticulocyte lysate, 0.5 μl amino acid mixture (containing 1 mM of each amino acid), 0.5 μl RNasin (40 U/μl), 4 μl water and 1 μl RNA (1 mg/μl).

The RNA was incubated for 2 minutes at 65° C. before adding it to the reaction mixture. The reaction was incubated for 60–90 minutes at 30° C. The reaction was stopped with 2 μl of a solution containing cycloheximide at a concentration of 0.2 mg/μl. In vitro translation samples were used either directly for the DNA priming/polymerase reactions (described in Examples 3 and 4 below) or they were frozen and stored at −70° C.

In vitro translation of the 3.1 kb RNA transcript produced by SP6-promoted transcription of the DHBV genome resulted in the formation of a major translation product of ~90 kd, as shown in FIG. 2. FIG. 2A shows the protein products obtained from in vitro translation reactions in the presence of $^{35}$S-methionine with RNA templates derived from p5.1Gal (See FIG. 1). The in vitro translation product of the 3.1 kb RNA encoding the DHBV polymerase gene product is shown in Lane 1, and the in vitro translation product from RNA purified from brome-mosaic (BMV), a control provided by the supplier of the translation kit, is shown in Lane 2. As can be seen from FIG. 2, Lane 1, in vitro translation of the 3.1 kb RNA transcript yielded a major protein product with a molecular weight of ~90 kd, as expected for the 836 amino acid-long polymerase gene product. See FIG. 1. The appearance of a second, more rapidly migrating protein product can be attributed to initiation at a second AUG codon, which is located 51 amino acids downstream of the first AUG of the polymerase open reading frame (Mandart et al., supra; see FIG. 1). It is believed that in vivo synthesis of the polymerase occurs from this second AUG (Chang et al., Nature, 337: 364–68 (1989); Schlicht et al., Cell, 56: 85–92 (1989)).

EXAMPLE 3

In Vitro Assay for DNA Priming Activity of In Vitro-Synthesized DHBV Polymerass Gene Product The in vitro transcription/translation product prepared according to the method set forth in Examples 1 and 2 above was assayed for DNA priming activity, according to the following methods. 5 μl of the in vitro translation mixture (not labelled with $^{35}$S-methionine) was combined with 1 μl 10X reaction buffer (500 mM Tris-HCl pH 7.5, 100 mM MgCl$_2$, 150 mM NaCl), 2.5 μl water and 0.5 μl $^{32}$P-dGTP (400 Ci/mmol, 10 μCi/μl, Amersham). The reaction was incubated typically for 30 minutes at 30° C. The reaction was stopped by addition of 180 μl of protein loading buffer (50 mM Tris-HCl, pH 6.8, 5% β-mercaptoethanol, 2% SDS, 0.1% bromophenol blue and 10% glycerol). An aliquot (18 μl) of the solution was electrophoresed through a 10% SDS-containing polyacrylamide gel. The gel was then dried and autoradiographed.

The results of the DNA priming assay can be seen in FIG. 2A, Lanes 3 and 4. Lane 3 shows the results of the priming assay using the DHBV polymerase translation product; and Lane 4 shows a control assay, wherein the in vitro translation product of brome mosaic virus (BMV) was tested for DNA priming activity as a negative control (this translation product should possess no priming activity, and therefore no $^{32}$P-labelled bands should appear in Lane 4). As can be seen from FIG. 2A, the in vitro-synthesized DHBV polymerase gene product possesses the DNA priming activity ascribed to the polymerase gene product in vivo, as demonstrated by the incorporation of labelled dGTP into the protein, resulting in the visible band upon autoradiography. The in vitro translation product of BMV displays no such incorporation of dGTP.

EXAMPLE 4

In Vitro Assay for Measuring Reverse Transcriptase Activity of In Vitro-Synthesized DHBV Polymerase Gene Product The in vitro-synthesized DHBV polymerase gene product prepared as described in Examples 1 and 2 was assayed for RNA-dependent DNA polymerase activity (i.e., reverse transcriptase activity) according to the following procedures. The DNA polymerase assay reaction mixture was assembled exactly as described for the DNA priming reaction of Example 3, except that 1 μl of water was replaced with a solution containing dATP, dCTP and TTP (142 μM of each). The $^{32}$P-labelled dGTP could be replaced with $^{32}$P dATP or dTTP, if desired. If this is done, the appropriate changes should be made with the dNTP solution so that all 4 dNTPs are available in the reaction mixture. Reactions were incubated at 30° C. for 30 minutes and stopped by the addition of protein loading buffer, as described in Example 3 above.

In an alternative procedure, DNA was synthesized in the presence of all 4 dNTPs without $^{32}$P-labelled dNTP. The product of the completed DNA polymerization reaction was then purified by incubation with RNaseA (65 mg/μl final concentration) for 10 minutes at 37° C., and subsequently with SDS (0.6%) and proteinase K (1 mg/ml) for 1 hour at 45° C. DNA was extracted twice with phenol, once with phenolchloroform and with a solution of butanol:isopropanol (7:3) in 20 μl of TE (10 mM Tris-HCl, pH 8, 0.1 mM EDTA) containing 5 mg/μl RNaseA and incubated at 37° C. for 20 minutes. DNA was visualized with the Southern hybridization procedure, according to well known methods.

The results of the reverse transcriptase assay are shown in FIG. 2B. The polymerase reactions were incubated for 0, 5, 10 and 30 minutes (Lanes 1–4) at 30° C. and for 10 minutes at 22° C., 37° C. and 60° C. (Lanes 5–7). Reactions shown in FIG. 2B were carried out in the presence of $^{32}$P-dATP. The radioactivity (CPM) in the polymerase bands was quantitated with an imager system (AMBIS).

As can be seen in FIG. 2B, the rate of nucleotide incorporation into the growing DNA strand occurs in a time- and temperature-dependent fashion, as would be expected from an enzymatic reaction, and is not restricted to dGTP as a substrate. Moreover, additional slow-migrating products were observed extending upward from the position corresponding to the polymerase protein to the top of the polyacrylamide gel (Lane 3). It has been verified that these products represent polymerase proteins attached to longer DNA strands of varying lengths. Since the linkage between the protein and the first nucleotide of the growing DNA strand resisted boiling in SDS (and also incubation in 1M KOH at 55° C., the results not shown herein), it is apparent that the protein-DNA bond is covalent.

The present invention is not limited to the embodiments specifically described and exemplified above, but is capable of variation and modification without departure from the scope of the appended claims.

What is claimed is:

1. A rapid, in vitro method for measuring the DAN priming activity of a hepadnavirus polymerase gene product, comprising the steps of:
   a) providing a substantially virus-free hepadnavirus polymerase gene product;
   b) providing an RNA template for hepadnavirus minus strand DNA synthesis which comprises a sequence capable of forming a stem-loop structure that includes a site for binding and priming of said hepadnavirus polymerase gene product;
   c) combining said hepadnavirus polymerase gene product and said RNA template for hepadnavirus minus strand DNA synthesis in an assay buffer with a detectably labeled nucleotide triphosphate comprising the first nucleotide incorporated into said hepadnavirus minus strand DNA, under conditions promoting DNA priming activity of said hepadnavirus polymerase gene product, resulting in the formation of a complex comprising said hepadnavirus polymerase gene product, said RNA template for minus strand DNA synthesis and said detectably labeled nucleotide triphosphate;
   d) separating said complex from said assay buffer; and
   e) detecting an amount of said detectably labeled nucleotide triphosphate in said separated complex, said amount being determinative of said DNA priming activity of said hepadnavirus polymerase gene product.

2. A method according to claim 1, wherein said hepadnavirus polymerase gene product and said RNA template for hepadnavirus minus strand DNA synthesis are provided together by in vitro transcription of a DNA molecule comprising said hepadnavirus polymerase gene to produce an RNA molecule encoding said hepadnavirus polymerase gene product, said RNA molecule serving as said RNA template for hepadnavirus minus strand DNA synthesis and further being translated to produce said hepadnavirus polymerase gene product.

3. A method according to claim 1, wherein said detectably labeled nucleotide triphosphate is selected from the group consisting of dGTP and analogs thereof.

4. A method according to claim 1, wherein said complex is separated from said assay buffer by gel electrophoresis.

5. A method according to claim 1, wherein said complex is separated from said assay buffer by immunological interaction with antibodies recognizing said hepadnavirus polymerase gene product.

6. A method according to claim 1, adapted for screening potential anti-hepadnaviral agents for their ability to inhibit DNA priming activity of a hepadnavirus polymerase gene product, comprising the steps of:
 a) preparing at least one test sample in a known volume of assay buffer, each said test sample comprising:
  i) a substantially virus-free hepadnavirus polymerase gene product;
  ii) an RNA template for hepadnavirus minus strand DNA synthesis which comprises a sequence capable of forming a stem-loop structure that includes a site for binding and priming of said hepadnavirus polymerase gene product; and
  iii) a potential anti-hepadnaviral agent;
 b) preparing a control sample in a volume equivalent to said known volume of assay buffer, said control sample comprising:
  i) a substantially virus-free hepadnavirus polymerase gene product; and
  ii) an RNA template for hepadnavirus minus strand DNA synthesis which comprises a sequence capable of forming a stem-loop structure that includes a site for binding and priming of said hepadnavirus polymerase gene product;
 c) contacting each said test sample and said control sample with equivalent amounts of a detectably labeled nucleotide triphosphate comprising the first nucleotide incorporated into said hepadnavirus minus strand DNA, under conditions promoting DNA priming activity of said hepadnavirus polymerase gene product, resulting in the formation of a complex comprising said polymerase gene product and said detectably labeled nucleotide triphosphate;
 d) separating said complex from said assay buffer in each said test sample and said control sample;
 e) detecting the amount of said detectably labeled nucleotide triphosphate in each said separated complex, said amount being determinative of said DNA priming activity of said hepadnavirus polymerase gene product; and
 f) comparing the respective amounts of said detectably labeled nucleotide triphosphate in said separated complexes of each said test sample and said control sample, a reduction in the amount of said detectably labeled nucleotide triphosphate in separated complexes of said test sample as compared to said control sample being indicative of inhibition of said DNA priming activity of said hepadnavirus polymerase gene product by said potential anti-hepadnaviral agent.

7. A rapid, in vitro method for measuring the reverse transcriptase activity of a hepadnavirus polymerase gene product, comprising the steps of:
 a) providing a substantially virus-free hepadnavirus polymerase gene product;
 b) providing an RNA template for hepadnavirus minus strand DNA synthesis which comprises a template sequence for said minus strand DNA, adjacent in a 3' direction to an initiation site for said minus strand DNA synthesis, and sequence capable of forming a stem-loop structure that includes a site for binding and priming of said hepadnavirus polymerase gene product;
 c) combining said hepadnavirus polymerase gene product and said RNA template for hepadnavirus minus strand DNA synthesis in an assay buffer with nucleotide triphosphates for DNA synthesis, under conditions promoting reverse transcriptase activity of said hepadnavirus polymerase gene product, thereby producing a nascent strand of DNA from said RNA template, said nascent DNA being part of a complex that further comprises said hepadnavirus polymerase gene product;
 d) separating said complex from said assay buffer; and
 e) detecting the amount of said nascent DNA, said amount being determinative of said reverse transcriptase activity of said hepadnavirus polymerase gene product.

8. A method according to claim 7, wherein said hepadnavirus polymerase gene product and said RNA template for hepadnavirus minus strand DNA synthesis are provided together by in vitro transcription of a DNA molecule comprising said hepadnavirus polymerase gene to produce an RNA molecule encoding said hepadnavirus polymerase gene product, said RNA molecule serving as said RNA template for hepadnavirus minus strand DNA synthesis and further being translated to produce said hepadnavirus polymerase gene product.

9. A method according to claim 7, wherein said nucleotide triphosphates for DNA synthesis are detectably labeled and selected from the group consisting of dATP, dCTP, dGTP, dTTP and analogs thereof.

10. A method according to claim 7, wherein said complex is separated from said assay buffer by gel electrophoresis.

11. A method according to claim 7, wherein said complex is separated from said assay buffer by immunological interaction with antibodies recognizing said hepadnavirus polymerase gene product.

12. A method according to claim 7, wherein said complex is rendered detectable during said combining step by providing one of said nucleotide triphosphates in the form of a detectably labeled nucleotide triphosphate analog, thereby producing a detectably labeled nascent DNA strand.

13. A method according to claim 7, wherein said complex is rendered detectable after said separating step.

14. A method according to claim 7, which further comprises the step of determining the length of said nascent DNA strand in said separated complex.

15. A method according to claim 7, wherein said hepadnavirus polymerase gene product is provided in a primed form by pre-incubating said hepadnavirus polymerase gene product with an RNA sequence capable of forming a stem-loop structure that includes a site for binding and priming of said hepadnavirus polymerase gene product, in a buffer containing nucleotide triphosphates incorporated into said primed form, under conditions promoting the DNA priming activity of said hepadnavirus polymerase gene product, thereby producing a primed form of said hepadnavirus polymerase gene product.

16. A method according to claim 7, adapted for screening potential anti-hepadnaviral agents for their ability to inhibit reverse transcriptase activity of a hepadnavirus polymerase gene product, comprising the steps of:
  a) preparing at least one test sample in a known volume of assay buffer, each said test sample comprising:
    i) a substantially virus-free hepadnavirus polymerase gene product;
    ii) an RNA template for hepadnavirus minus strand DNA synthesis which comprises a template sequence for said minus strand DNA, adjacent in a 3' direction to an initiation site for said minus strand DNA synthesis, and sequence capable of forming a stem-loop structure that includes a site for binding and priming of said hepadnavirus polymerase gene product; and
    iii) a potential anti-hepadnaviral agent;
  b) preparing a control sample in a volume equivalent to said known volume of assay buffer, said control sample comprising:
    i) a substantially virus-free hepadnavirus polymerase gene product; and
    ii) an RNA template for hepadnavirus minus strand DNA synthesis which comprises a template sequence for said minus strand DNA, adjacent in a 3' direction to an initiation site for said minus strand DNA synthesis, and sequence capable of forming a stem-loop structure that includes a site for binding and priming of said hepadnavirus polymerase gene product;
  c) contacting each said test sample and said control sample with equivalent amounts of nucleotide triphosphates for DNA synthesis, under conditions promoting reverse transcriptase activity of said hepadnavirus polymerase gene product, thereby producing a nascent strand of DNA from said RNA template, said nascent DNA being part of a complex that further comprises said hepadnavirus polymerase gene product;
  d) separating said complex from said assay buffer in each said test sample and said control sample;
  e) detecting the amount of said nascent DNA in each said separated complex, said amount being determinative of said reverse transcriptase activity of said hepadnavirus polymerase gene product; and
  f) comparing the respective amounts of nascent DNA in said separated complexes of each said test sample and said control sample, a reduction in the amount of said nascent DNA in separated complexes of said test sample as compared to said control sample being indicative of inhibition of said reverse transcriptase activity of said hepadnavirus polymerase gene product by said potential anti-hepadnaviral agent.

17. A rapid, in vitro method for screening potential anti-hepadnaviral agents for their ability to inhibit DNA priming activity of a hepadnavirus polymerase gene product, comprising the steps of:
  a) preparing a control sample and at least one test sample in a known volume of assay buffer, said control sample and each said test sample including an enzymatically active composition of matter comprising, in extracellular combination, a hepadnavirus polymerase gene product and an RNA template for hepadnavirus minus strand DNA synthesis, both produced by expression, in a non-hepadnavirus system, of an isolated DNA sequence encoding said hepadnavirus polymerase gene product, each said test sample further including a predetermined amount of a potential anti-hepadnaviral agent;
  b) contacting each said test sample and said control sample with equivalent amounts of a detectably labeled nucleotide triphosphate comprising the first nucleotide incorporated into said hepadnavirus minus strand DNA, under conditions promoting DNA priming activity of said hepadnavirus polymerase gene product, resulting in the formation of a complex comprising said hepadnavirus polymerase gene product and said detectably labeled nucleotide triphosphate;
  c) separating said complex from said assay buffer in each said test sample and said control sample;
  d) detecting the amount of said detectably labeled nucleotide triphosphate in each said separated complex, said amount being determinative of said DNA priming activity of said hepadnavirus polymerase gene product; and
  e) comparing the respective amounts of said detectably labeled nucleotide triphosphate in said separated complexes of each said test sample and said control sample, a reduction in the amount of said detectably labeled nucleotide triphosphate in separated complexes of said test sample as compared to said control sample being indicative of inhibition of said DNA priming activity of said hepadnavirus polymerase gene product by said potential anti-hepadnaviral agent.

18. A rapid, in vitro method for screening potential anti-hepadnaviral agents for their ability to inhibit reverse transcriptase activity of a hepadnavirus polymerase gene product, comprising the steps of:
  a) preparing a control sample and at least one test sample in a known volume of assay buffer, said control sample and each said test sample including an enzymatically active composition of matter comprising, in extracellular combination, a hepadnavirus polymerase gene product and an RNA template for hepadnavirus minus strand DNA synthesis, both produced by expression, in a non-hepadnavirus system, of an isolated DNA sequence encoding said hepadnavirus polymerase gene product, each said test sample further including a predetermined amount of a potential anti-hepadnaviral agent;
  b) contacting each said test sample and said control sample with equivalent amounts of nucleotide triphosphates for DNA synthesis, under conditions promoting reverse transcriptase activity of said hepadnavirus polymerase gene product, thereby producing a nascent strand of DNA from said RNA template, said nascent DNA being part of a complex that further comprises said hepadnavirus polymerase gene product;
  c) separating said complex from said assay buffer in each said test sample and said control sample;
  d) detecting the amount of said nascent DNA in each said separated complex, said amount being determinative of said reverse transcriptase activity of said hepadnavirus polymerase gene product; and
  e) comparing the respective amounts of nascent DNA in said separated complexes of each said test sample and said control sample, a reduction in the amount of said nascent DNA in separated complexes of said test sample as compared to said control sample being indicative of inhibition of said reverse transcriptase activity of said hepadnavirus polymerase gene product by said potential anti-hepadnaviral agent.

* * * * *